United States Patent
Brister et al.

(10) Patent No.: US 7,081,096 B2
(45) Date of Patent: Jul. 25, 2006

(54) TEMPERATURE MAPPING BALLOON

(75) Inventors: Mark Brister, Forestville, CA (US); Dave Thompson, Andover, MN (US); James Carney, Eden Prairie, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 269 days.

(21) Appl. No.: 10/351,162

(22) Filed: Jan. 24, 2003

(65) Prior Publication Data

US 2004/0147852 A1    Jul. 29, 2004

(51) Int. Cl.
*A61B 5/00* (2006.01)
(52) U.S. Cl. ...................................... 600/549
(58) Field of Classification Search ........ 600/433–435, 600/466, 473, 474, 505, 549, 585, 374; 604/264, 604/523; 374/100, 137; 606/41, 34; 607/105, 607/43, 122, 99
See application file for complete search history.

(56) References Cited

U.S. PATENT DOCUMENTS

| | | | |
|---|---|---|---|
| 4,490,421 A | 12/1984 | Levy | 428/36.9 |
| 4,682,605 A * | 7/1987 | Hoffman | 600/549 |
| 4,762,129 A | 8/1988 | Bonzel | 606/194 |
| 4,811,598 A * | 3/1989 | Dillier et al. | 374/136 |
| 5,451,233 A | 9/1995 | Yock | 606/194 |
| 5,840,030 A | 11/1998 | Ferek-Petric et al. | 600/439 |
| 5,871,449 A | 2/1999 | Brown | 600/474 |
| 5,871,483 A * | 2/1999 | Jackson et al. | 606/41 |
| 5,924,997 A | 7/1999 | Campbell | 600/474 |
| 6,245,026 B1 | 6/2001 | Campbell et al. | 600/549 |
| 6,366,799 B1 | 4/2002 | Acker et al. | 600/424 |
| 6,432,062 B1 * | 8/2002 | Ren et al. | 600/549 |
| 2001/0047138 A1 | 11/2001 | Kokate et al. | 600/585 |
| 2002/0077564 A1 * | 6/2002 | Campbell et al. | 600/549 |
| 2002/0082515 A1 | 6/2002 | Campbell et al. | 600/549 |
| 2002/0087208 A1 * | 7/2002 | Koblish et al. | 607/113 |
| 2003/0120271 A1 * | 6/2003 | Burnside et al. | 606/41 |
| 2003/0171691 A1 * | 9/2003 | Casscells et al. | 600/549 |

* cited by examiner

Primary Examiner—Max F. Hindenburg
Assistant Examiner—Brian Szmal

(57) ABSTRACT

The temperature mapping balloon of the present invention provides a device for locating inflammation and increased metabolic activity associated with conditions such as vulnerable plaque, by mapping temperature of a body lumen, such as an artery or blood vessel. The temperature mapping balloon comprises a balloon with a thermal mapping coating disposed on the inside or outside of the balloon. The thermal mapping coating can be a thermochromic coating that changes color in response to temperature or a sensor coating comprising a plurality of temperature sensors.

17 Claims, 8 Drawing Sheets

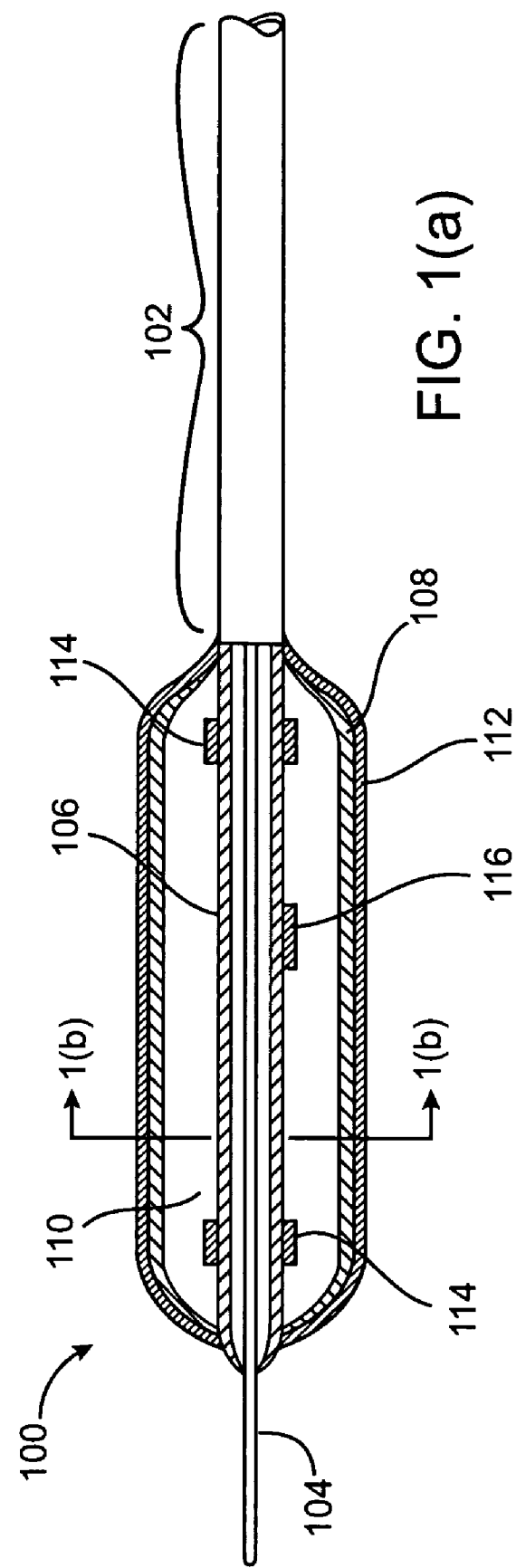

TEMPERATURE MAPPING BALLOON

TECHNICAL FIELD

The technical field of this disclosure is medical devices, particularly, a balloon for mapping temperature of a body lumen, such as an artery or blood vessel.

BACKGROUND OF THE INVENTION

Heart disease, specifically coronary artery disease, is a major cause of death, disability, and healthcare expense in the United States and other industrialized countries. Until recently, most heart disease was considered the result of a progressive increase of hard plaque in the coronary arteries. The commonly held theory postulated that an atherosclerotic disease process of hard plaques led to a critical narrowing (stenosis) of the affected coronary artery to produce anginal syndromes, commonly known as chest pain. The progression of the arterial narrowing reduced blood flow, triggering blood clot formation. The blood clot might choke off the flow of oxygen rich blood (ischemia) to heart muscles, causing a heart attack, or alternatively, the blood clot might break from the vessel wall and lodge in another organ vessel, such as the brain, causing a thrombotic stroke.

Within the past decade, evidence has emerged challenging this model of atherosclerosis, coronary artery disease, and heart attacks. While the build up of hard plaque may produce angina and severe ischemia in the coronary arteries, new clinical data now suggests that the rupture of sometimes non-occlusive, vulnerable plaques causes the vast majority of heart attacks. The rate of heart attacks due to vulnerable plaques is estimated as high as 60 to 80 percent. In many instances vulnerable plaques do not impinge on the vessel lumen, but are like an abscess ingrained beneath the arterial wall. For this reason, conventional angiography or fluoroscopy techniques that indicate vessel flow area are unlikely to detect the vulnerable plaque. Due to the difficulty of detection and lack of symptoms such as angina, vulnerable plaques may be more dangerous than other plaques that cause pain. Currently, no strategy exists for reliably identifying vulnerable plaques.

Formation and rupture of vulnerable plaques can result in heart attack and/or stroke. The majority of vulnerable plaques include a lipid pool, smooth muscle (endothelial) cells, and a dense infiltrate of macrophages, all contained by a thin fibrous cap. The lipid pool is believed to form because of pathological processes involving low density lipoprotein (LDL), macrophages, and the inflammatory process. The macrophages oxidize the LDL producing foam cells. The macrophages, foam cells, and associated endothelial cells release various substances, such as tumor necrosis factor, tissue factor, and matrix proteinases, which result in generalized cell necrosis and apoptosis, pro-coagulation, and weakening of the fibrous cap. The inflammation process may weaken the fibrous cap to the extent that mechanical stress, such as that produced by increased blood pressure, may result in rupture. The lipid core and other contents of the vulnerable plaque may then spill into the blood stream thereby initiating a clotting cascade. The cascade produces a blood clot (thrombosis) that potentially results in a heart attack and/or stroke. The process is exacerbated due to the release of collagen and plaque components, e.g., collagen and tissue factor, which enhance clotting upon their release.

Balloon catheters are used in a variety of medical therapeutic applications including intravascular angioplasty. For example, a balloon catheter device is inflated during PTCA (percutaneous transluminal coronary angioplasty) to dilate a stenotic blood vessel. After inflation, the pressurized balloon exerts a compressive force on the lesion thereby increasing the inner diameter of the affected vessel. Some exemplary balloon catheters are disclosed in U.S. Pat. No. 4,490,421 to Levy, U.S. Pat. No. 5,451,233 to Yock, and U.S. Pat. No. 4,762,129 to Bonzel, incorporated herein by reference.

Vulnerable plaque typically is detected by sensing elevated temperature in the vulnerable plaque relative to the surrounding tissue. The elevated temperature results from the inflammation of and the increased metabolic activity in the vulnerable plaque. The temperature increase may be from a fraction of a degree to a few degrees Celsius, e.g., from 0.1–0.2 degrees Celsius to 1.25–1.65 degrees Celsius. Existing temperature sensing systems use pinpoint sized temperature sensors with a small surface area, which only sense a very small area of the vessel wall tissue and may easily overlook vulnerable plaque lesions. While these sensors may be adequate to detect vulnerable plaque when the sensors actually touch the vulnerable plaque, they typically miss a large portion of the arterial wall. Reliable detection of a vulnerable plaque lesion is not assured.

Existing temperature sensing systems have additional limitations. Typical sensors such as thermisters are discrete units fastened to a catheter or balloon. Such sensors are expensive and cost may limit the number of sensors that are used, limiting the resolution of the temperature mapping: current practice is to disregard the circumferential temperature variation and concentrate on the longitudinal variation to reduce the number of sensors. This may miss a vulnerable plaque localized to a partial circumference of the vessel. Use of discrete thermal sensors also results in the need to bring one or more wires from each thermal sensor to the outside of the patient during testing. This increases the size of the catheter lead and fabrication expenses.

U.S. Pat. No. 5,871,449 to Brown discloses a system for locating inflamed plaque including a catheter with an expander, the expander being operable to move a carrier transmitting infrared radiation into contact with the arterial wall.

U.S. Pat. No. 5,924,997 to Campbell discloses an intravascular catheter system capable of mapping thermal variations in the temperature of athrosclerotic plaque, incorporating a plurality of thermal sensors fixedly attached along the catheter's multi-lumen flexible tubular member.

U.S. Pat. No. 6,245,026 to Campbell et al. discloses a variety of thermal mapping catheters capable of sensing and mapping thermal variations in body vessels, in vascular applications the catheters being capable of detecting temperature variations in athrosclerotic plaque.

U.S. Patent application publication Ser. No. US 2001/0047138 to Kokate et al. discloses a method and device for detecting vulnerable plaque including an elongate shaft, a substrate fixed to the elongate shaft, and a plurality of sensors disposed on the substrate.

U.S. Patent application publication Ser. No. US 2002/0082515 to Campbell et al. discloses interventional tools suitable for measuring the temperature or temperature variations in a vessel wall and thereafter treating vulnerable plaque that is identified during the thermal mapping.

It would be desirable to have a temperature mapping balloon that would overcome the above disadvantages.

SUMMARY OF THE INVENTION

One aspect of the present invention provides a temperature mapping balloon able to reliably detect vulnerable plaque.

Another aspect of the present invention provides a temperature mapping balloon able to map temperature over the whole vessel wall.

Another aspect of the present invention provides a temperature mapping balloon able to sense small regions of vulnerable plaque.

Another aspect of the present invention provides a temperature mapping balloon using inexpensive temperature sensors.

Another aspect of the present invention provides a temperature mapping balloon using fewer electrical leads.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 1(a) & 1(b) show longitudinal and transverse cross sections, respectively, of a temperature mapping balloon made according to the present invention.

DETAILED DESCRIPTION OF THE PRESENTLY PREFERRED EMBODIMENT

The temperature mapping balloon of the present invention provides a device for locating inflammation and increased metabolic activity associated with conditions such as vulnerable plaque, by mapping temperature of a body lumen, such as an artery or blood vessel. The temperature mapping balloon comprises a balloon with a thermal mapping coating disposed on the inside or outside of the balloon. The thermal mapping coating can be a thermochromic coating that changes color in response to temperature or a sensor coating comprising a plurality of temperature sensors.

Figure 1B:
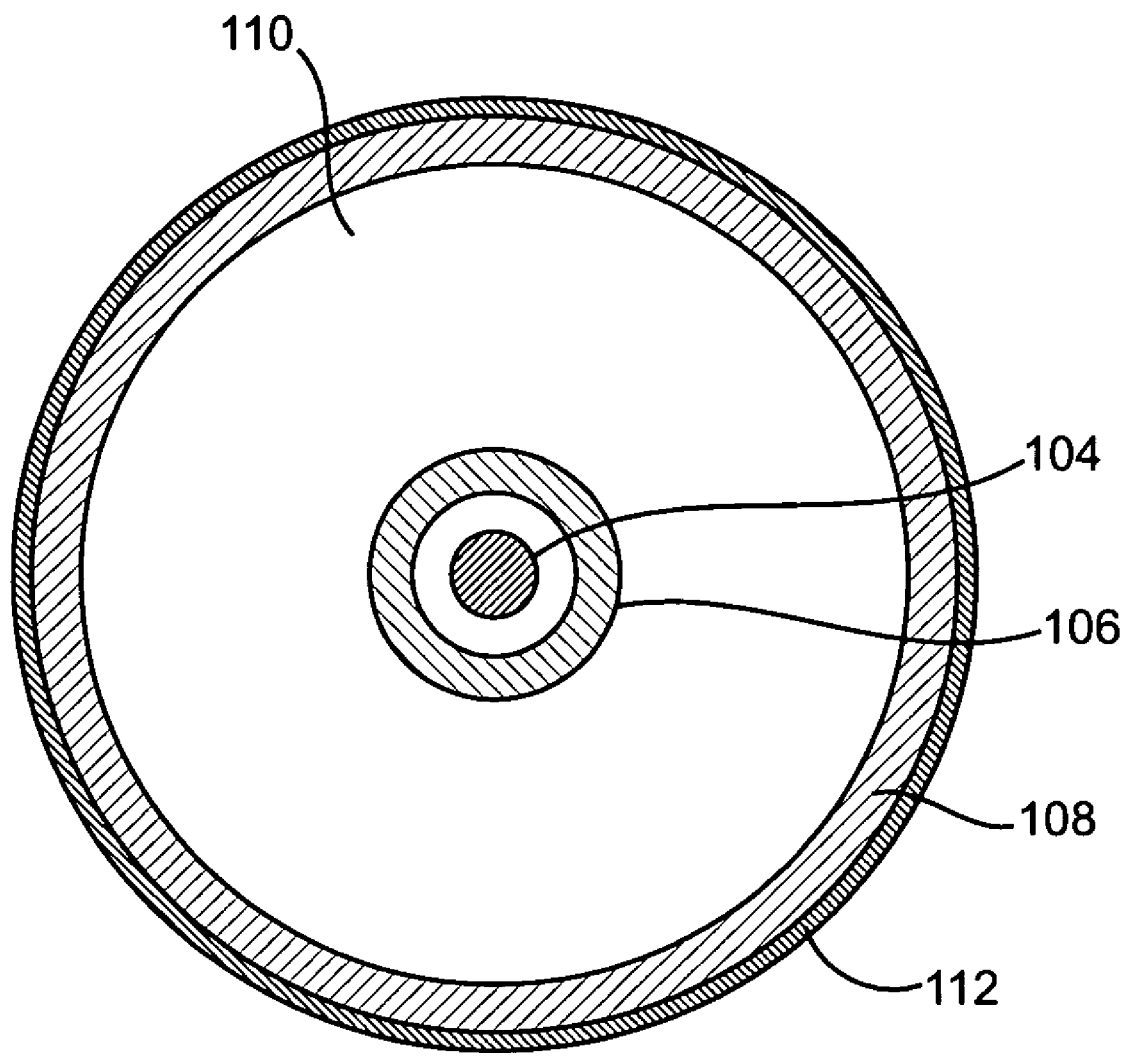

FIGS. 1(a) & 1(b) show longitudinal and transverse cross sections, respectively, of a temperature mapping balloon made according to the present invention. The temperature mapping balloon 100 is attached to a catheter lead 102, which positions the balloon 100 within the vessel and connects the balloon 100 to the outside of the patient for balloon inflation or signal transmission. The balloon 100 can be used with a guidewire 104 to assist in positioning the balloon 100, although those skilled in the art will appreciate that the balloon 100 can also be used without a guidewire if desired. The balloon 100 can be a polymer balloon as typically used for stent placement or the like, and made of nylon or Pebax® polyether-block co-polyamide polymers from ATOFINA Chemicals, Inc. or any other acceptable material.

The temperature mapping balloon 100 comprises an inner sleeve 106 and outer sleeve 108 forming a balloon lumen 110, and a thermal mapping coating 112 operably connected to the outer sleeve 108. The inner sleeve 106 provides a central aperture for the guidewire 104. The outer sleeve 108 is compliant and is expanded to the vessel wall when making a temperature map. The outer sleeve 108 can be flexible so that it conforms to the vessel wall without too great pressure in the balloon lumen 110. It is desirable to avoid too great pressure on vessel walls where vulnerable plaque may be present to avoid rupture of any vulnerable plaques present and release of the lipid core to the blood stream. The balloon lumen 110 communicates to the exterior of the patient through the catheter lead 102 and is filled with pressurized fluid to expand the balloon 100 through stretching the outer sleeve 108.

The thermal mapping coating 112 can be a thermochromic or sensor coating sensitive to temperature. The thermochromic coating can change state as a function of temperature so that the vessel wall two-dimensional temperature map can be read visually or by optical scanning machine from the thermochromic coating after the balloon 100 is withdrawn from the vessel. The sensor coating can provide an electrical parameter, such as resistance or voltage, varying locally as a function of temperature. A plurality of local electrical signals responsive to the local electrical parameters are transmitted from the sensor coating through the catheter lead 102 and converted to a two-dimensional temperature map readable by the physician. Those skilled in the art will appreciate that the thermal mapping coating 112 can be disposed on the exterior or interior of the outer sleeve 108, or can be sandwiched between layers of the outer sleeve 108 if the outer sleeve 108 comprises a plurality of layers. The particular placement of the thermal mapping coating 112 can depend on the degree of isolation desired between the thermal mapping coating 112 and the vessel wall, and the thermal sensitivity desired.

Radiopaque markers can be provided to indicate the position of the temperature mapping balloon 100 radiologically. Longitudinal markers 114 indicate the proximal and distal ends of the temperature sensing portion of the balloon 100. Radial markers 116 indicate the rotational position of the balloon 100 relative to the vessel. Various indicia can be used so that the radial markers 116 can be read radiologically. For example, two asymmetric characters such as "2" and "5" could be placed 90 degrees apart on the inner sleeve 106. In another example, a circle could be placed on the inner sleeve 106. The radiopaque markers can also be disposed on or in the outer sleeve 108 to provide more distance from the axis of the balloon 100 and greater precision. The radiopaque marker can be a circumferential and longitudinal grid on the outer sleeve 108 with indicia of longitudinal measure on the longitude and indicia of degrees on the circumference. Those skilled in the art will appreciate that many marker arrangements are possible to provide an indication of the longitudinal and rotational position of balloon 100 within the vessel.

Alternatively, radio-frequency (RF) coils may be provided with the balloon 100 to indicate the position of the temperature mapping balloon 100 within the patient. The miniature coil may be mounted on or within the catheter body, on or near the balloon 100. The location of the coil and the balloon may be determined using external detection mechanisms and triangulation, as substantially described in U.S. Pat. No. 6,366,799 to Acker et al. and incorporated herein by reference.

In yet another alternative, ultrasonic marker transponders may be provided with the balloon 100 to indicate the position of the temperature mapping balloon 100 within the patient. The transponders may be mounted on or within the catheter body, on or near the balloon 100. The location of the distal end of the catheter and the balloon may be determined using external detection mechanisms and triangulation as substantially described in U.S. Pat. No. 5,840,030 to Ferek-Petric et al. and incorporated herein by reference.

Figure 2:
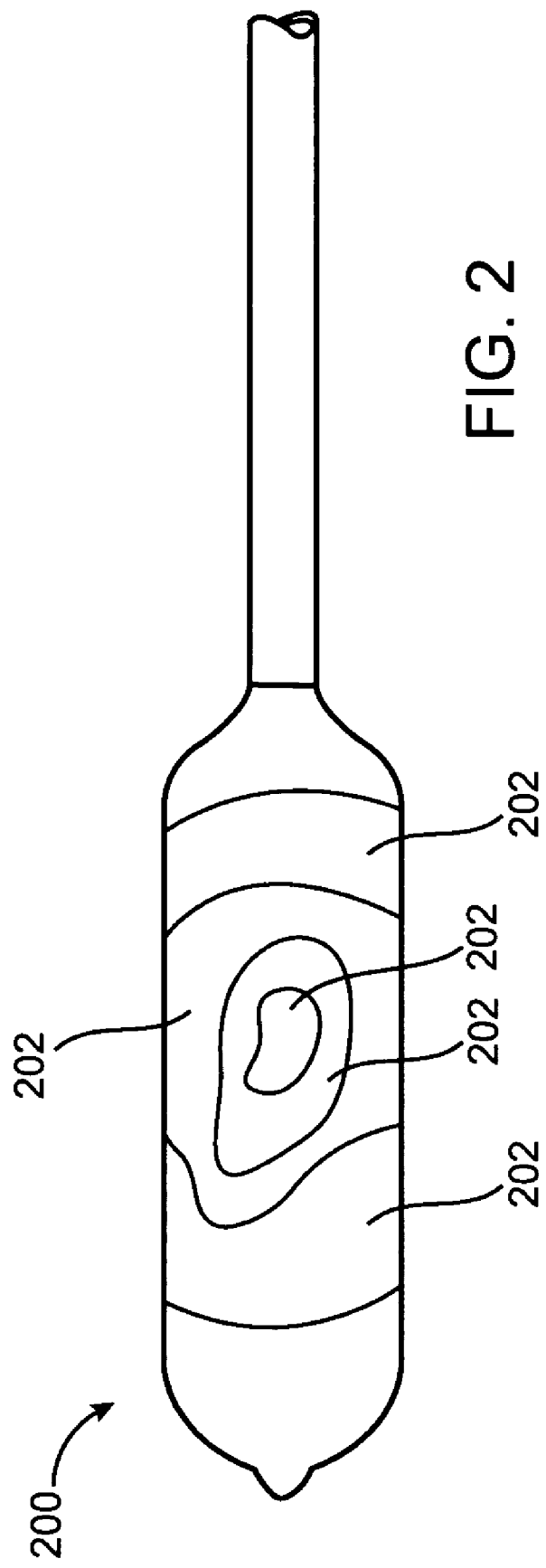
FIG. 2 shows a side view of a thermochromic temperature mapping balloon made according to the present invention.

FIG. 2 shows a side view of a thermochromic temperature mapping balloon made according to the present invention. A temperature sensing substance that changes color as a function of temperature can be provided as the thermal mapping coating on or within the temperature mapping balloon 200. The thermal mapping coating is a thermochromic coating, i.e., the coating changes color as a function of temperature. The thermochromic coating over the balloon 200 can be uniform or can be a plurality of discrete dots. Before use, the exterior of the balloon 200 appears as a uniform color. The balloon 200 is inserted into the vessel of the patient to the position where vulnerable plaque is suspected. The balloon 200 is inflated to contact the vessel wall and held in position for the time required for the temperature sensing substance to change color to reflect the temperature of the vessel wall. The balloon 200 is deflated and withdrawn from the patient. The balloon 200 can be re-inflated to the size previously used in the vessel, or another size as desired, to facilitate reading the temperature map. The balloon 200 displays isothermal temperature regions 202 as different colors providing a two-dimensional map of the temperature of the vessel wall. The physician can use the map information to pinpoint where therapy should be provided, both longitudinally and circumferentially. The definition between the isothermal temperature regions 202, the number of the isothermal temperature regions 202, and the specific colors of the isothermal temperature regions 202 will depend on the particular temperature sensing substance used. In another embodiment, the re-inflated balloon 200 can be inserted in an optical scanning machine on removal from the patient and the optical scanning machine can read and record the isothermal temperature regions 202 providing a two-dimensional map of the temperature of the vessel wall. The optical scanning machine can also convert the colors to digital data, which can be manipulated to provide easily interpretable information, such as isothermal lines, temperature gradient profiles, numerical readouts, or other forms as desired.

The temperature sensing substance can be any substance which changes color in the desired temperature range. Because vessel wall temperature is typically 0.65 degrees Celsius above oral temperature in human subjects, and the vulnerable plaque can raise the vessel wall temperature less than about 0.2 degrees to about 1.65 degrees Celsius, the temperature sensing substance can change colors at about 37 to 41 degrees Celsius with a sensitivity of about 0.1 degrees Celsius. The temperature sensing substances can be reversible or irreversible, i.e., the color change can be temporary or permanent. For reversible temperature sensing substances, the temperature sensing substance remains in the changed state long enough for the balloon to be removed from the patient and the two-dimensional map read. Depending on the compatibility of the various materials, the temperature sensing substance can be mixed in with the balloon or coating material directly, or microencapsulated to isolate the temperature sensing substance. Such temperature sensing substances are well known in the art and commercially available.

Examples of temperature sensing substances suitable for this application include, but are not limited to, thermochromic substances which are active substances or state change substances. Active substances include organic substances, such as dyes or pigments, which react chemically to change color with temperature. Examples of active substances are leuco dyes and substances such as those used in temperature recording decals made by Telatemp Corporation.

State change substances include substances which change color as a function of temperature with changes in phase, crystalline state, or crystalline structure. The state change can also induce a chemical reaction. Phase change substances include substances that make a visually perceptible change from a solid to a liquid, such as the temperature indicating wax used in the Tempilstik® temperature indicating crayon made by Tempil, Inc. Another example is the material used in the Thermostripe indicating label manufactured by Hallcrest, Inc., which provides irreversible temperature indication. Crystalline state change substances include substances that change color due to material change, such as the change in the amount of twist in and reflectivity of a liquid crystal. An example is the material used in the reversible liquid crystal temperature indicator devices using liquid crystals available from Hallcrest, Inc. Another example is liquid crystals which are organic compounds derived from esters of cholesterol and micro-encapsulated in gelatin spheres. Crystalline structure change substances include substances that change color as the crystalline state changes and may undergo several state and color changes in a given temperature range. A series of different colors can also be produced by mixing different thermochromic substances with each changing color at a different temperature. Those skilled in the art will appreciate that the classifications of temperature sensing substances above are for illustration only and that the particular substance may fit in more than one class.

Figure 3A:
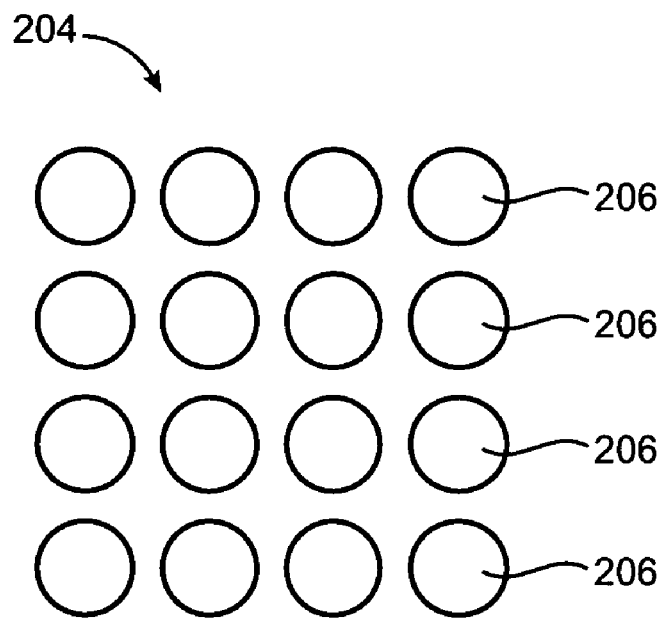
FIGS. 3(a) & 3(b) show detailed views of one embodiment of a thermochromic temperature mapping balloon using bistable dots made according to the present invention.
Figure 3B:
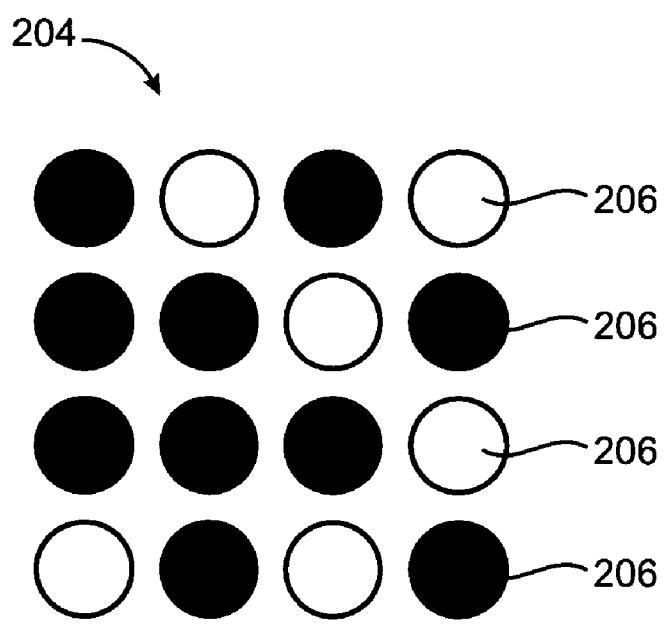

FIGS. 3(a) & 3(b) show detailed views of one embodiment of a thermochromic temperature mapping balloon using bistable dots made according to the present invention. FIG. 3(a) shows the bistable dots before exposure to vessel temperature. FIG. 3(a) shows a 4×4 array 204 of bistable dots 206, which are a portion of a thermal mapping coating on or within the temperature mapping balloon. The array 204 can be repeated as desired to cover the balloon 200. The bistable dots 206 can be miniscule so as to appear as a continuous coating to the unaided eye or can be macroscopic, appearing as discrete dots. The number, size, shape, and spacing of the bistable dots 206 in array 204 can be selected for the desired degree of temperature mapping detail and practical manufacturing considerations.

The bistable dots 206 can be designed to change color at a predetermined threshold temperature. An example of a bistable dot is the temperature sensitive indicating dots used in the Tempa(dot)DOT™ thermometers manufactured by 3M Company. The predetermined threshold temperature for each of the bistable dots 206 in the array 204 can be selected so that the array 204 changes colors as the temperature increases, i.e., more of the bistable dots 206 reach their predetermined threshold temperature and change color as the temperature increases. The bistable dots with threshold temperatures close to each other can be distributed throughout the array to make the array color change appear gradual. The bistable dots 206 can all start at one color and change to another single color, such as from tan to blue. In another embodiment, the bistable dots 206 can all start at one color and change to a variety of colors, giving the impression of a number of colors from the visual perception of the combination of colors within the array. FIG. 3(*b*) shows the bistable dots after exposure to temperature, so that a number of the bistable dots 206 have exceeded their threshold temperature and have changed color.

The 4×4 array 204 is exemplary only: a 4×4 array can provide a four degree Celsius temperature range if the bistable dots reach their predetermined threshold temperature in 0.25 degree increments. A four degree Celsius temperature range can cover the typical human body temperature of 37 degrees Celsius to a vulnerable plaque high temperature of 41 degrees Celsius. Different size arrays and bistable dot threshold temperature increments can be selected to cover different temperature ranges with different degrees of sensitivity. The array can also use geometric arrangements other than a regular Cartesian grid, such as unequal rectangular grids, concentric circles, asymmetric arrays, or other arrays as desired. The array can be irregular when the balloon is deflated and regular when the balloon is inflated. Those skilled in the art will appreciate that many array patterns can be used as desired.

Those skilled in the art will appreciate that the temperature sensing substance can be applied as a thermal mapping coating on or within the temperature mapping balloon by a number of conventional methods. For uniform coatings, the thermal mapping coating can be applied to the balloon by dipping, spraying, painting, wiping, rolling, printing, silk screening, deposition, or combinations thereof. For non-uniform coatings, such as the bistable dot coating, the thermal mapping coating can be applied to the balloon by spraying with a mask, micro-spraying, inkjet spraying, printing, pad printing, inkjet printing, photolithography, dot matrix printing, vapor deposition, or combinations thereof. Additional coatings, such as parylene, silicone rubber, polytetrafluoroethylene, various polyurethanes, or various plastics, can be applied over the thermal mapping coating to assure biocompatibility and avoid irregularities that could lead to thrombosis formation. The coatings can be applied with the temperature mapping balloon inflated or deflated, as suitable for the particular coatings selected.

Figure 4:
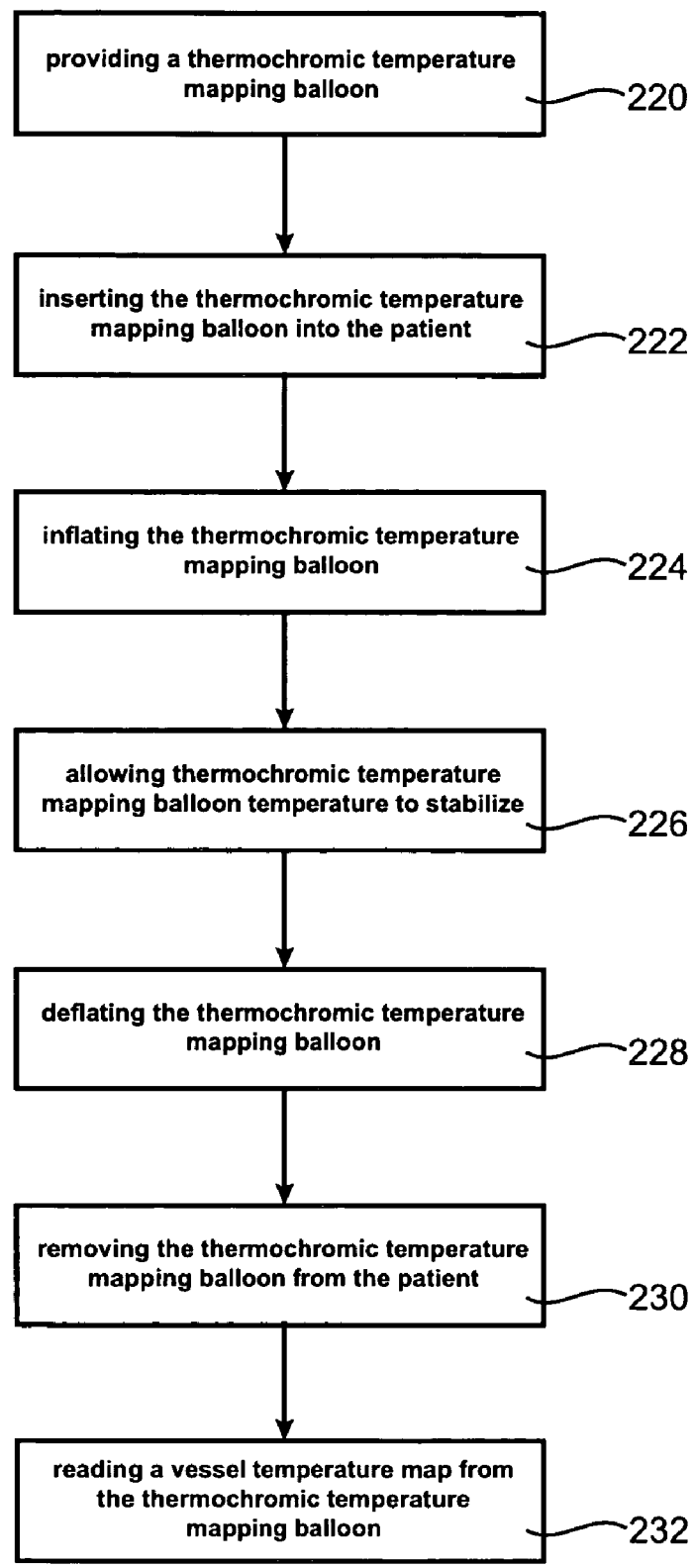
FIG. 4 shows a flow chart of a method of use for a thermochromic temperature mapping balloon made according to the present invention.

FIG. 4 shows a flow chart of a method of use for a thermochromic temperature mapping balloon made according to the present invention. A thermochromic temperature mapping balloon is provided at 220 and inserted in the patient at 222. The balloon is inflated at 224. After the temperature of the balloon stabilizes at 226, the balloon is deflated at 228 and removed from the patient at 230. A vessel temperature map is read from the balloon at 232.

At 220, a thermochromic temperature mapping balloon is provided. The thermochromic temperature mapping balloon can include or be coated with a temperature sensing substance that changes color as a function of temperature. The distribution of the temperature sensing substance can be uniform or discrete.

The thermochromic temperature mapping balloon is inserted in the patient at 222. The balloon is inserted into the vessel of the patient to the position where vulnerable plaque is suspected or anywhere a temperature map is desired. For application in the coronary vessels, a catheter can be inserted through the patient's femoral artery, a guide wire inserted thorough the catheter, and the balloon moved into position along the guide wire. Those skilled in the art will appreciate that the method described is not limited to coronary applications and can be used in any body lumen where it is desirable to obtain a temperature map.

The thermochromic temperature mapping balloon is inflated at 224 to contact the vessel wall and held in position to allow the temperature of the thermochromic temperature mapping balloon to stabilize at 226. The thermochromic temperature mapping balloon is deflated 228 and removed from the patient 230.

A vessel temperature map is read from the thermochromic temperature mapping balloon at 232. The balloon can be re-inflated as desired to facilitate reading the vessel temperature map. The balloon displays isothermal temperature regions as different colors providing a two-dimensional map of the temperature of the vessel wall. In one embodiment, the vessel temperature map can be read visually. In another embodiment, the vessel temperature map can be read with an optical scanning machine. The optical scanning machine can also convert the colors to digital data, which can be analyzed to provide easily interpretable information, such as isothermal lines, temperature gradient profiles, numerical readouts, or other forms as desired.

Figure 5A:
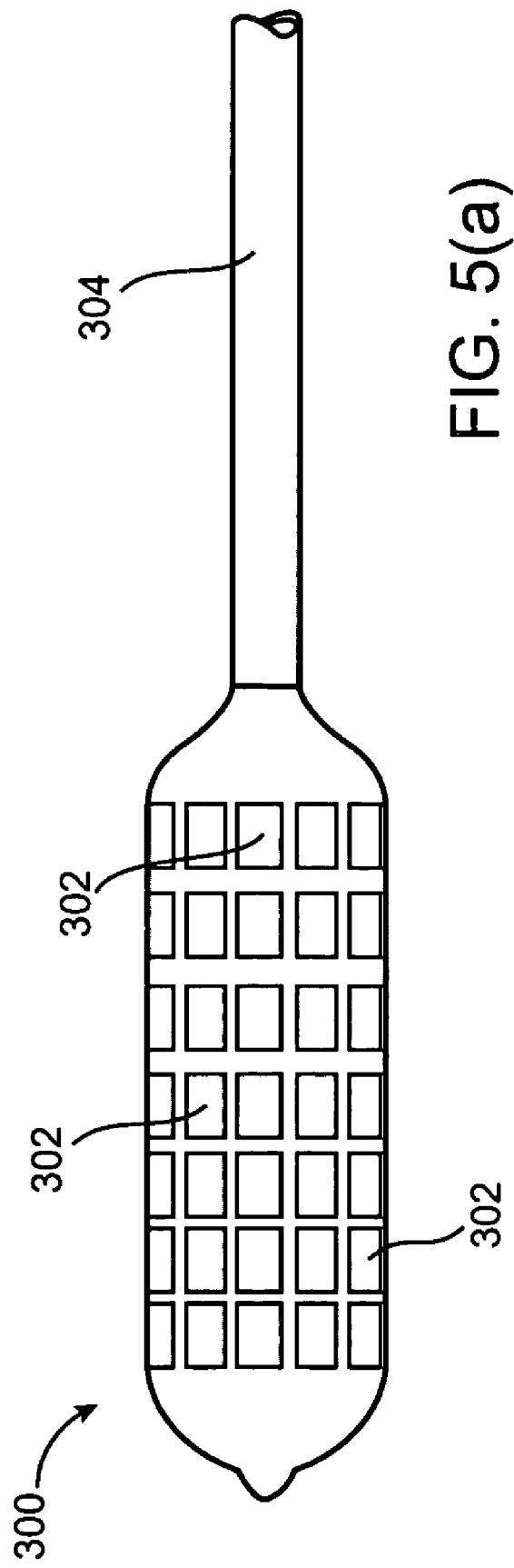
FIGS. 5(a) & 5(b) show a side view and detailed view, respectively, of a sensor coated temperature mapping balloon made according to the present invention.
Figure 5B:
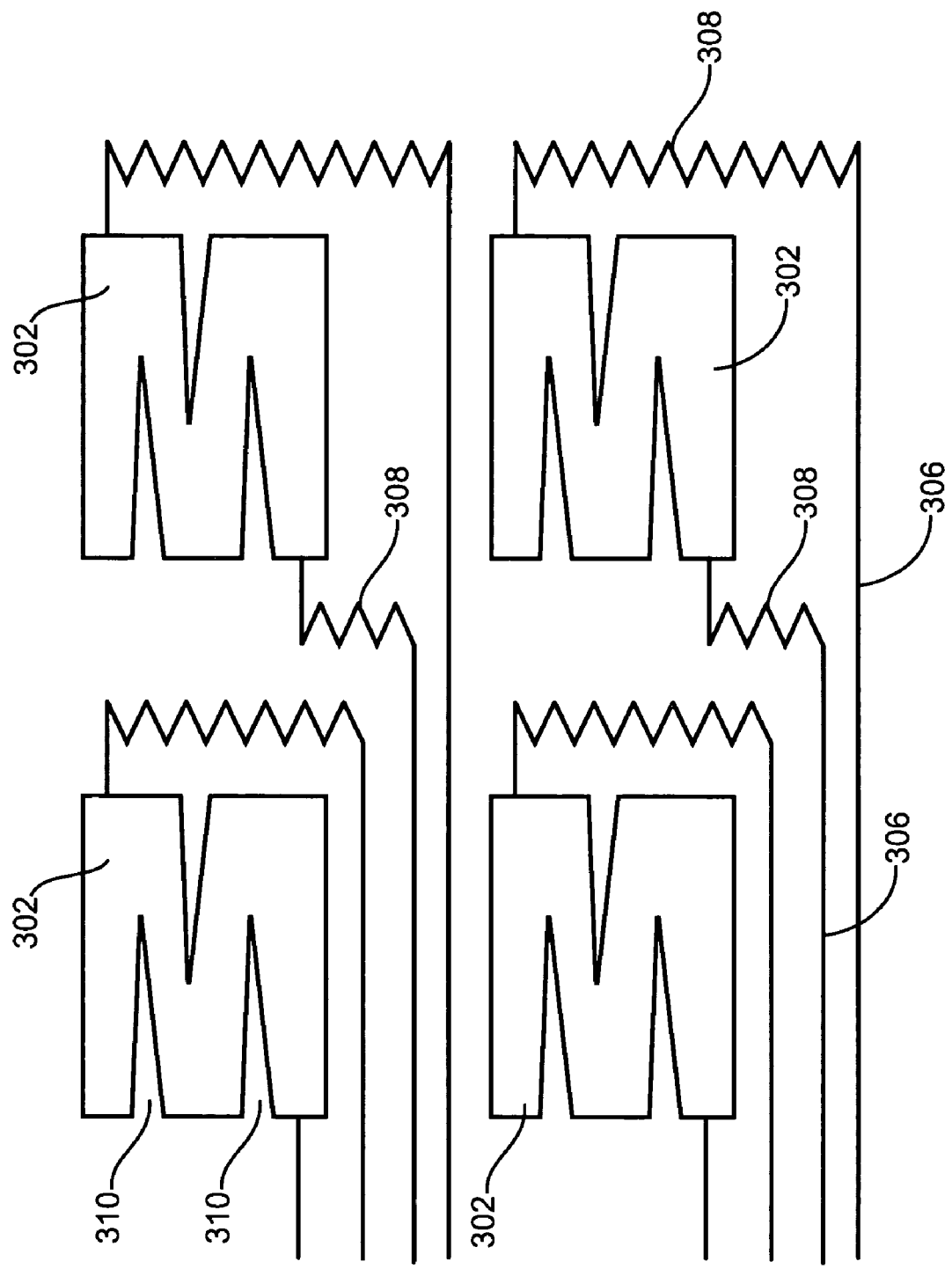

FIGS. 5(*a*) & 5(*b*), in which like elements share like reference numbers, show a side view and detailed view, respectively, of a sensor circuit coated temperature mapping balloon made according to the present invention. A plurality of temperature sensors 302 arranged in a Cartesian array or other pattern as desired can be provided as a thermal mapping coating on or within the temperature mapping balloon 300. The balloon 300 is inserted into the vessel of the patient to a position where vulnerable plaque is suspected. The balloon 300 is inflated to contact the vessel wall and held in position for the time required to obtain a stable temperature reading over the vessel wall.

The data from the temperature sensors 302 can be transmitted along the catheter lead 304 through conductors 306 and then manipulated to provide easily interpretable information, such as isothermal lines, temperature gradient profiles, numerical readouts, or other forms as desired. Those skilled in the art will appreciate that numerous wiring configurations are possible depending on the type of temperature sensors used and the particular wiring configuration desired. The conductors can have common grounds or power supplies. The conductors can cross each other with the provision of insulating layers between the conductors. The conductors can be connected to multiplexing circuitry to reduce the number of wires running along the catheter lead.

The temperature sensors 302 and conductors 306 can be made of a variety of materials such as nickel, copper, platinum, chromium, iron, rhodium, aluminum, conducting graphite polymers, and alloys and combinations thereof. If the temperature sensors 302 and conductors 306 are disposed on the outside of the balloon, an electrical insulating layer of a material such as parylene, silicone rubber, polytetrafluoroethylene, various polyurethanes, or various plastics, can be used to prevent short circuits through contact with blood or vessel walls. In another embodiment, a second balloon can be disposed over the temperature sensors 302 and conductors 306 for electrical insulation.

The temperature sensors 302 can be any temperature sensor suitable for application as a thermal mapping coating. The temperature sensors 302 can be thermocouples, thermisters, resistance thermometers, resistive temperature detectors (RTDs), thermal piles, PN junctions, and the like. In one embodiment, the temperature sensors 302 can have a sensitivity of about 0.01 degrees Celsius in the range of temperatures from 20 to 40 degrees Celsius.

To maintain electrical continuity through the temperature sensors 302 and conductors 306 as the balloon expands, the sensor coating can include strain relieving features. Strain relieving cuts 310 can be provided in the temperature sensors 302 and accordion pleats 308 can be provided in the conductors 306. As the balloon expands, the strain relieving cuts 310 relieving strain in the temperature sensors 302 and accordion pleats 308 open relieving strain in the conductors 306. Because balloons typically expand radially more than longitudinally, such strain relieving features are primarily required in a radial direction. Strain relieving features can also be use in the longitudinal direction as desired.

Figure 6:
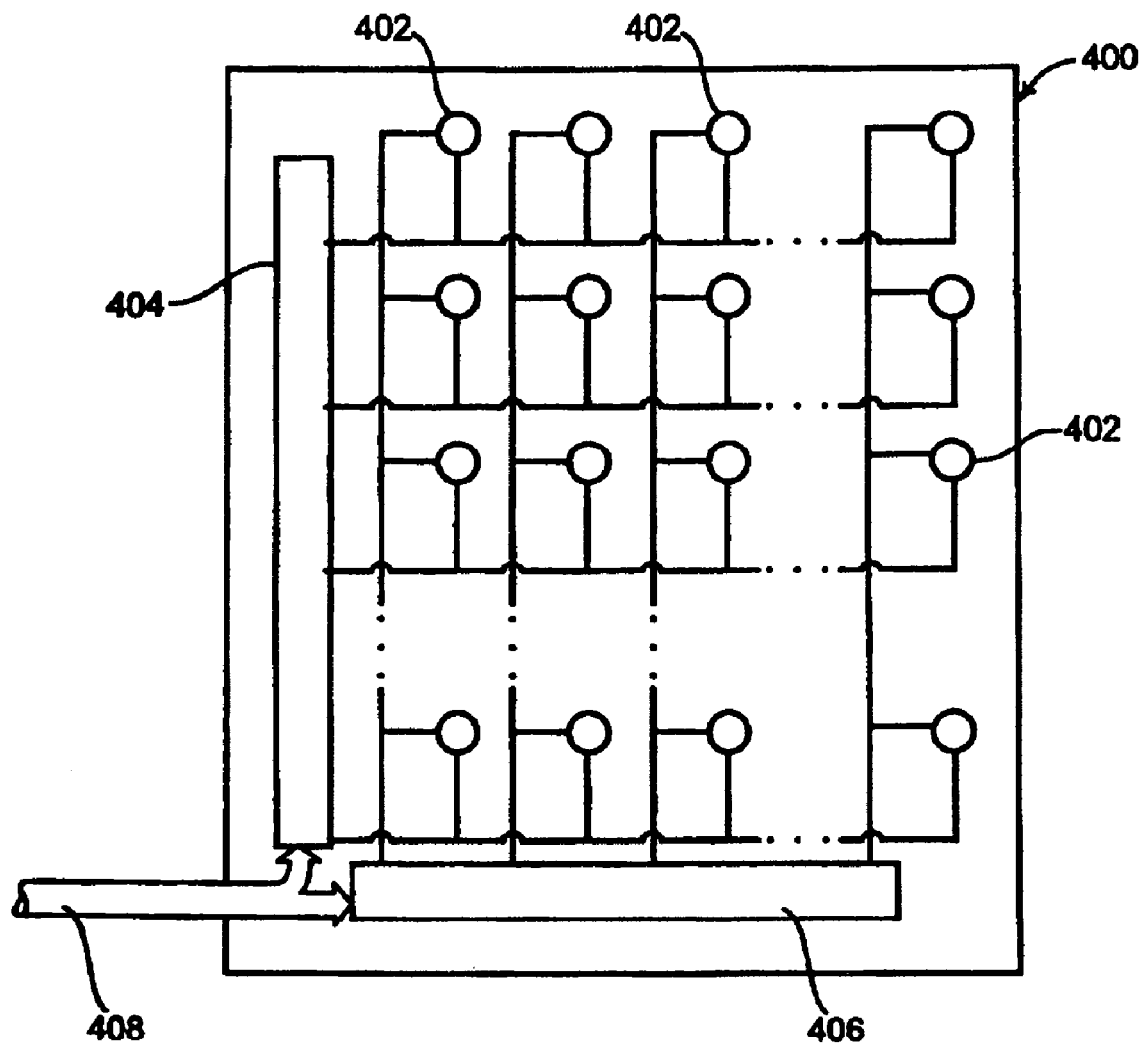
FIG. 6 shows a diagram of a sensor coated temperature mapping balloon made according to the present invention.

FIG. 6 shows a diagram of a sensor coated temperature mapping balloon made according to the present invention. In this embodiment, the temperature sensors and conductors are arranged for multiplexing the signals to reduce the number of wires required. A plurality of temperature sensors 402 is disposed as a thermal mapping coating on or within the temperature mapping balloon 400. Each of the plurality of temperature sensors 402 is operably connected to a row address circuit 404 and a column address circuit 406. In one embodiment, the row address circuit 404 and column address circuit 406 can be disposed on or within the temperature mapping balloon 400. In another embodiment, the row address circuit 404 and column address circuit 406 can be disposed in the catheter lead. In response to an interrogation signal on bus 408, the row address circuit 404 and column address circuit 406 interrogate one of the plurality of temperature sensors 402 and returns a temperature signal for the particular temperature sensor on bus 408. Those skilled in the art will appreciate that the arrangement of the plurality of temperature sensors is exemplary only and that the plurality of temperature sensors can be arranged in other groups without departing from the spirit and scope of the present invention.

Those skilled in the art will appreciate that the sensor coating can be applied as a thermal mapping coating on or within the temperature mapping balloon by a number of conventional methods. The thermal mapping coating can be applied to the balloon by vapor deposition, electrostatic deposition, spraying with a mask, micro-spraying, inkjet spraying, printing, pad printing, inkjet printing, photolithography, dot matrix printing, or combinations thereof. Additional coatings, such as parylene, silicone rubber, polytetrafluoroethylene, various polyurethanes, or various plastics, can be applied over the thermal mapping coating to provide electrical insulation, assure biocompatibility, and avoid irregularities that could lead to thrombosis formation. The coatings can be applied with the temperature mapping balloon inflated or deflated, as suitable for the particular coatings selected. The surface of the balloon can be treated to be hydrophilic or hydrophobic as suited to the particular coating material.

In one embodiment, the sensor coating can be applied to thin sheet of plastic or similar material, then the thin sheet affixed to the inside or outside of the balloon. Longitudinal cuts can be made in the thin sheet in order to allow for expansion as the balloon is inflated. If affixed to the inside of the balloon, the thin sheet can be installed by wrapping the thin sheet around a spindle, then placing the balloon around the thin sheet and the spindle. If affixed to the outside of the balloon, the thin sheet can be applied with the sensor coating between the thin sheet and the balloon, so that the thin sheet provides an electrical insulating layer preventing short circuits. In another embodiment, a second sheet can be affixed to the side of the thin sheet bearing the sensor coating to provide ease of handling and protect the sensor coating.

It is important to note that FIGS. 1–6 illustrate specific applications and embodiments of the present invention, and is not intended to limit the scope of the present disclosure or claims to that which is presented therein. For example, the thermal mapping coating can be embedded within the balloon. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A temperature mapping balloon for use in a vessel having a vessel wall comprising:
    a balloon, the balloon being conformable over the vessel wall; and
    a thermal mapping coating, the thermal mapping coating disposed on the balloon and comprising a sensor coating, the sensor coating comprising a plurality of temperature sensors.

2. The temperature mapping balloon of claim 1 wherein the thermal mapping coating is disposed in a location selected from the group consisting of outside the balloon and inside the balloon.

3. The temperature mapping balloon of claim 1 further comprising a position indicator disposed on the balloon.

4. The temperature mapping balloon of claim 3 wherein the position indicator is selected from the group consisting of radiopaque markers, radio-frequency (RF) coils, and ultrasonic marker transponders.

5. The temperature mapping balloon of claim 1 further comprising an insulating layer disposed on the sensor coating.

6. The temperature mapping balloon of claim 5 wherein the insulating layer is a material selected from the group consisting of parylene, silicone rubber, polytetrafluoroethylene, polyurethane, and plastic.

7. The temperature mapping balloon of claim 1 wherein the sensor coating is made of materials selected from the group consisting of nickel, copper, platinum, chromium, iron, rhodium, aluminum, conducting graphite polymers, and alloys and combinations thereof.

8. The temperature mapping balloon of claim 1 wherein the temperature sensors are selected from the group consisting of thermocouples, thermisters, resistance thermometers, resistive temperature detectors (RTDs), PN junctions, and thermal piles.

9. The temperature mapping balloon of claim 1 wherein each of the plurality of temperature sensors provides a temperature signal, and the temperature signals from the plurality of temperature sensors are multiplexed.

10. A method of using a temperature mapping balloon with a patient comprising:
    providing a thermochromic temperature mapping balloon, the thermochromic temperature mapping balloon comprising a plurality of arrays, each of the plurality of arrays comprises a plurality of bistable dots, the bistable dots change from one color to another color in response to a threshold temperature, and the threshold temperatures for the bistable dots in each of the plurality of arrays are distributed over a temperature range;
    inserting the thermochromic temperature mapping balloon into the patient;

inflating the thermochromic temperature mapping balloon;

allowing thermochromic temperature mapping balloon temperature to stabilize;

deflating the thermochromic temperature mapping balloon;

removing the thermochromic temperature mapping balloon from the patient; and reading a vessel temperature map from the temperature mapping balloon.

11. The method of claim 10 wherein reading a vessel temperature map comprises reading the vessel temperature map visually.

12. The method of claim 10 wherein reading a vessel temperature map comprises reading the vessel temperature map with an optical scanning machine.

13. The method of claim 12 wherein the optical scanning machine converts the vessel temperature map to digital data.

14. A temperature mapping balloon comprising:

a balloon; and a thermal mapping coating, the thermal mapping coating disposed on the balloon and comprising a sensor coating, the sensor coating comprising a plurality of temperature sensors;

wherein the sensor coating includes strain relieving features selected from the group consisting of strain relieving cuts and accordion pleats.

15. A temperature mapping balloon comprising:

a balloon; and a thermal mapping coating, the thermal mapping coating disposed on the balloon, and comprising a thermochromic coating;

wherein the thermochromic coating comprises a plurality of arrays, each of the plurality of arrays comprises a plurality of bistable dots, the bistable dots change from one color to another color in response to a threshold temperature, and the threshold temperatures for the bistable dots in each of the plurality of arrays are distributed over a temperature range.

16. The temperature mapping balloon of claim 15 wherein the thermochromic coating is readable by a method selected from the group consisting of visual reading and optical scanning machine reading.

17. The temperature mapping balloon of claim 15 wherein a substance for the thermochromic coating is selected from the group consisting of active substances, state change substances, phase change substances, crystalline state change substances, and crystalline structure change substances.

* * * * *